United States Patent
Liu et al.

(10) Patent No.: US 10,550,409 B2
(45) Date of Patent: Feb. 4, 2020

(54) DRIMENOL SYNTHASES III

(71) Applicant: Firmenich SA, Geneva (CH)

(72) Inventors: Eric Wen-Bo Liu, Shanghai (CN); Xiu-Feng He, Shanghai (CN); Olivier Haefliger, Geneva (CH); Zong-Xia Yu, Shanghai (CN); Pan Li, Shanghai (CN)

(73) Assignee: Firmenich SA, Meyrin (CH)

( * ) Notice: Subject to any disclaimer, the term of this patent is extended or adjusted under 35 U.S.C. 154(b) by 0 days.

(21) Appl. No.: 15/772,567

(22) PCT Filed: Nov. 7, 2016

(86) PCT No.: PCT/EP2016/076874
§ 371 (c)(1),
(2) Date: May 1, 2018

(87) PCT Pub. No.: WO2017/077125
PCT Pub. Date: May 11, 2017

(65) Prior Publication Data
US 2019/0093131 A1   Mar. 28, 2019

(30) Foreign Application Priority Data
Nov. 5, 2015   (WO) ................. PCT/CN2015/093897

(51) Int. Cl.
*C12P 7/02*   (2006.01)
(52) U.S. Cl.
CPC ......... *C12P 7/02* (2013.01); *C12Y 301/07007* (2013.01)

(58) Field of Classification Search
None
See application file for complete search history.

(56) References Cited

U.S. PATENT DOCUMENTS

| | | | |
|---|---|---|---|
| 2014/0259223 A1* | 9/2014 | Bouwmeester | C12N 9/0004 800/279 |
| 2015/0059018 A1* | 2/2015 | Bouwmeester | C12N 9/0004 800/278 |
| 2018/0208948 A1* | 7/2018 | Daviet | C12P 7/02 |
| 2018/0251797 A1* | 9/2018 | Zhang | C12N 9/16 |

FOREIGN PATENT DOCUMENTS

WO   2013058655 A1   4/2013

OTHER PUBLICATIONS

Guo et al., "Protein tolerance to random amino acid change", Proceedings of the National Academy of Sciences USA, vol. 101, No. 25, pp. 9205-9210, 2004 (Year: 2004).*

(Continued)

*Primary Examiner* — Richard C Ekstrom
(74) *Attorney, Agent, or Firm* — Armstrong Teasdale LLP

(57) ABSTRACT

The present invention discloses a method of producing drimenol and/or drimenol derivatives by contacting a polypeptide with farnesyl pyrophosphate. Also provided is an amino acid sequence of a polypeptide useful in the methods of the invention and nucleic acid encoding the polypeptides of the invention. The method further provides host cells or organisms genetically modified to express the polypeptides of the invention and useful to produce drimenol and/or drimenol derivatives.

10 Claims, 4 Drawing Sheets
Specification includes a Sequence Listing.

(56) References Cited

OTHER PUBLICATIONS

GenEmbl Accession No. HM807407, published Dec. 13, 2010 (Year: 2010).*
International Search Report from PCT Application No. PCT/EP2016/076874, dated Feb. 1, 2017.
Moonhyuk et al., "Molecular cloning and characterization of drimenol synthase from valerian plant (*Valeriana officinalis*)," Febs Letters, vol. 588, No. 24, pp. 4597-4603, 2014.
Accession No. E5GAG1—Martin et al., "Functional annotation, genome organization and phylogeny of the grapevine (*Vitis vinifera*) terpene synthase gene family based on genome assembly, FLcDNA cloning and enzyme assays," BMC Plant Biology, Biomed Central, London GB, vol. 10, No. 1, p. 226, 2010.

* cited by examiner

SEQUENCE LISTING

<160> NUMBER OF SEQ ID NOS: 7

<210> SEQ ID NO 1
<211> LENGTH: 1677
<212> TYPE: DNA
<213> ORGANISM: Paeonia anomala

<400> SEQUENCE: 1

```
atgtctcttc ccgtctcagt agctaatcag ccaccggcga aatgtaaaca agaggttatt    60
cgcaatacag caaatttccc ccgtggtatt tccgctcatc agttcatcac ttacactcct   120
caagatgagg aaactcgtgc gcatatagta caagagattg aagaactgaa agaaattgta   180
agaacagagg tgatgacact tgttggtata ccttcacaac aactcaagct tgttgatgca   240
atccaacgcc ttggtgtggg ataccacttt cagaaggaga tagatgaagc cttacaccaa   300
ctgtatgata catatggtca tggccaagat gaagatctct tcacagttgc tctttggttc   360
agacttctaa gacaacaagg gtataatgtt tcatgtgaca tattcaacaa attcaccgac   420
gacaagggaa acttcaagga atgcttggtt caaaatgtgg agggcatggt agccttgtac   480
gaagcaacgc atctcagagt gcatggagaa gatgtacttg aagcagcact cacttttaca   540
accattcacc ttaaggcctt ggcaactcat cttgcaagcc atcccttag agcactagtg    600 aatcgtgccc tagaacagcc tacctataag ggtgtaccta ggctggaggc aagacattat   660
atatctttct atcaacaaga gcaattgcat gataaagctt tactgagact tgccaagtta   720
gattttaacc tactacaatc attgcacaaa aaggagctat cggaggtcgc tagatggtgg   780
acaaaagtaa acttttgaaaa caagttacct ttcgtgagag acagggtggt ggagagttac   840
ttttggggat tgggagatta ttttgagcct gagcactcca ttgctagaat gatattaagc   900
aaaataatcg ccctagtaac ggttatggat gatatttatg acgcatatgg tacactggaa   960
gaactcgagc tatttacaga tgcagttcaa aggtgggata tcaactgcac ccaacaactc   1020
ccagaataca ttaaagtgtt ttttcaggca atgttagatg catacgaaga gattgaagaa   1080
gaattatcta acgaacctgg acgaacatat cgtgttcatt atgcaataga agccatgaaa   1140
atacaagccc aagcataccc tgctgaaaca aaatggtcta atgaaaagta tgtaccgaca   1200
tttgaggagt atatggataa tgcacgatta agcgcaggtt acttcatgct tacagtcata   1260
tcttttcttt ttatggggga agacgcgaca aaagattcat ttgattggct gttcaacgac   1320
cctaagattc ttagagcctc atcaatcatt accaggctca tggatgacat agtttctcat   1380
aagtttgagc aagagagagg acatgttgca tcatccgttg agtgttacat gaagcaacac   1440
aatgtttcgg agcaacaaac atatcaagag tttcaaatga aaattgtgga gggatggaaa   1500
gatctaaatc aggcattact catacctact gatgcatcga ttcctctcct tactcgtatc   1560
cttaatttta cacgctttat ggatgttaac tacaaggaac gagatgaatt cacacatgtt   1620
ggagacgttt taaaagatcg aattgcattg ttactaattg atcccatccc aatatga     1677
```

<210> SEQ ID NO 2

<211> LENGTH: 558
<212> TYPE: PRT
<213> ORGANISM: Paeonia anomala

<400> SEQUENCE: 2

```
Met Ser Leu Pro Val Ser Val Ala Asn Gln Pro Pro Ala Lys Cys Lys
1               5                   10                  15

Gln Glu Val Ile Arg Asn Thr Ala Asn Phe Pro Arg Gly Ile Ser Ala
            20                  25                  30

His Gln Phe Ile Thr Tyr Thr Pro Gln Asp Glu Thr Arg Ala His
        35                  40                  45

Ile Val Gln Glu Ile Glu Leu Lys Glu Ile Val Arg Thr Glu Val
50                  55                  60

Met Thr Leu Val Gly Ile Pro Ser Gln Gln Leu Lys Leu Val Asp Ala
65                  70                  75                  80

Ile Gln Arg Leu Gly Val Gly Tyr His Phe Gln Lys Glu Ile Asp Glu
                85                  90                  95

Ala Leu His Gln Leu Tyr Asp Thr Tyr Gly His Gly Gln Asp Glu Asp
            100                 105                 110

Leu Phe Thr Val Ala Leu Trp Phe Arg Leu Leu Arg Gln Gln Gly Tyr
        115                 120                 125

Asn Val Ser Cys Asp Ile Phe Asn Lys Phe Thr Asp Asp Lys Gly Asn
130                 135                 140

Phe Lys Glu Cys Leu Val Gln Asn Val Glu Gly Met Val Ala Leu Tyr
145                 150                 155                 160

Glu Ala Thr His Leu Arg Val His Gly Glu Asp Val Leu Glu Ala Ala
                165                 170                 175

Leu Thr Phe Thr Thr Ile His Leu Lys Ala Leu Ala Thr His Leu Ala
            180                 185                 190

Ser His Pro Leu Arg Ala Leu Val Asn Arg Ala Leu Glu Gln Pro Thr
        195                 200                 205

Tyr Lys Gly Val Pro Arg Leu Glu Ala Arg His Tyr Ile Ser Phe Tyr
210                 215                 220

Gln Gln Glu Gln Leu His Asp Lys Ala Leu Leu Arg Leu Ala Lys Leu
225                 230                 235                 240

Asp Phe Asn Leu Leu Gln Ser Leu His Lys Lys Glu Leu Ser Glu Val
                245                 250                 255

Ala Arg Trp Trp Thr Lys Val Asn Phe Glu Asn Lys Leu Pro Phe Val
            260                 265                 270

Arg Asp Arg Val Val Glu Ser Tyr Phe Trp Gly Leu Gly Asp Tyr Phe
        275                 280                 285

Glu Pro Glu His Ser Ile Ala Arg Met Ile Leu Ser Lys Ile Ile Ala
290                 295                 300

Leu Val Thr Val Met Asp Asp Ile Tyr Asp Ala Tyr Gly Thr Leu Glu
305                 310                 315                 320

Glu Leu Glu Leu Phe Thr Asp Ala Val Gln Arg Trp Asp Ile Asn Cys
                325                 330                 335

Thr Gln Gln Leu Pro Glu Tyr Ile Lys Val Phe Phe Gln Ala Met Leu
            340                 345                 350

Asp Ala Tyr Glu Glu Ile Glu Glu Leu Ser Asn Glu Pro Gly Arg
        355                 360                 365

Thr Tyr Arg Val His Tyr Ala Ile Glu Ala Met Lys Ile Gln Ala Gln
370                 375                 380

Ala Tyr Leu Ala Glu Thr Lys Trp Ser Asn Glu Lys Tyr Val Pro Thr
```

```
            385                 390                 395                 400
Phe Glu Glu Tyr Met Asp Asn Ala Arg Leu Ser Ala Gly Tyr Phe Met
                405                 410                 415

Leu Thr Val Ile Ser Phe Leu Phe Met Gly Glu Asp Ala Thr Lys Asp
                420                 425                 430

Ser Phe Asp Trp Leu Phe Asn Asp Pro Lys Ile Leu Arg Ala Ser Ser
                435                 440                 445

Ile Ile Thr Arg Leu Met Asp Asp Ile Val Ser His Lys Phe Glu Gln
450                 455                 460

Glu Arg Gly His Val Ala Ser Ser Val Glu Cys Tyr Met Lys Gln His
465                 470                 475                 480

Asn Val Ser Glu Gln Gln Thr Tyr Gln Glu Phe Gln Met Lys Ile Val
                485                 490                 495

Glu Gly Trp Lys Asp Leu Asn Gln Ala Leu Leu Ile Pro Thr Asp Ala
                500                 505                 510

Ser Ile Pro Leu Leu Thr Arg Ile Leu Asn Phe Thr Arg Phe Met Asp
                515                 520                 525

Val Asn Tyr Lys Glu Arg Asp Glu Phe Thr His Val Gly Asp Val Leu
                530                 535                 540

Lys Asp Arg Ile Ala Leu Leu Leu Ile Asp Pro Ile Pro Ile
545                 550                 555
```

<210> SEQ ID NO 3
<211> LENGTH: 543
<212> TYPE: DNA
<213> ORGANISM: Artificial Sequence
<220> FEATURE:
<223> OTHER INFORMATION: The DNA sequence of CaMV35S promoter

<400> SEQUENCE: 3

```
gaattcccat ggagtcaaag attcaaatag aggacctaac agaactcgcc gtaaagactg      60
gcgaacagtt catacagagt ctcttacgac tcaatgacaa gaagaaaatc ttcgtcaaca     120
tggtggagca cgacacgctt gtctactcca aaaatatcaa agatacagtc tcagaagacc     180
aaagggcaat tgagactttt caacaaaggg taatatccgg aaacctcctc ggattccatt     240
gcccagctat ctgtcacttt attgtgaaga tagtggaaaa ggaaggtggc tcctacaaat     300
gccatcattg cgataaagga aaggccatcg ttgaagatgc ctctgccgac agtggtccca     360
aagatggacc cccacccacg aggagcatcg tggaaaaaga agacgttcca accacgtctt     420
caaagcaagt ggattgatgt gatatctcca ctgacgtaag ggatgacgca caatcccact     480
atccttcgca agacccttcc tctatataag gaagttcatt tcatttggag aggacagggt     540
acc                                                                   543
```

<210> SEQ ID NO 4
<211> LENGTH: 213
<212> TYPE: DNA
<213> ORGANISM: Artificial Sequence
<220> FEATURE:
<223> OTHER INFORMATION: The DNA sequence of OCS terminator

<400> SEQUENCE: 4

```
ctgcaggcat gccctgcttt aatgagatat gcgagacgcc tatgatcgca tgatatttgc      60
tttcaattct gttgtgcacg ttgtaaaaaa cctgagcatg tgtagctcag atccttaccg     120
ccggtttcgg ttcattctaa tgaatatatc acccgttact atcgtatttt tatgaataat     180
attctccgtt caatttactg attgtccaag ctt                                  213
```

<210> SEQ ID NO 5
<211> LENGTH: 1140
<212> TYPE: DNA
<213> ORGANISM: Artificial Sequence
<220> FEATURE:
<223> OTHER INFORMATION: The optimized DNA sequence of GgFPS

<400> SEQUENCE: 5

```
atgcaaccac accatcatca caaagaagga agaatgcaca agtttactgg agttaacgca      60
aagtttcaac agcctgctct cagaaatctt tctcctgttg tggttgaaag agagagggaa     120
gagtttgtgg attttttccc tcaaattgtt agagatttga ctgaagatgg aatcggtcat     180
ccagaagtgg gagatgcagt tgctaggctc aaggaagttt acagtataa tgctcctgga      240
ggtaaatgta acagaggact cacagtggtt gctgcataca gggaattatc tggaccaggt     300
caaaaggatg ctgagtcact tagatgtgca ttggctgtgg atggtgcat cgagcttttc      360
caggcatttt tcttggttgc tgatgatatt atggatcaat cactcaccag aaggggacag     420
ttatgttggt ataagaaaga aggagttggt cttgatgcta ttaatgatag ttttcttttg     480
gagtcttcag tgtacagagt tttgaagaaa tattgtagac aaaggcctta ctacgttcat     540
ctcttagaac ttttcttgca aactgcatac cagacagagt tgggacagat gctcgatctt     600
attacagctc cagtgtcaaa ggttgatctc tcacacttta gtgaagagag atataaggca     660
atcgttaagt acaaaaccgc tttctacagt ttctaccttc ctgtggctgc tgctatgtat     720
atggttggta tagattctaa ggaagagcat gaaaacgcaa aagctatact tttggaaatg     780
ggagagtact ccaaatacag ggatgattac cttgattgct tcggagatcc tgctttgacc     840
ggaaaggttg gtactgatat ccaagataat aagtgttctt ggctcgtggt tcaatgctta     900
cagagagtta caccgaaca aggcagctc ttagaggata actatggaag aaaggaacca      960
gagaaagtgg caaaggttaa agaattgtac gaggctgttg gtatgagagc agctttccaa    1020
cagtatgaag agagttctta cagaaggctt caagaattga tcgagaaaca ctcaaacaga    1080
ctccctaaag aaatcttcct cggactcgct cagaaaatct acaaaggca aaaatgataa    1140
```

<210> SEQ ID NO 6
<211> LENGTH: 30
<212> TYPE: DNA
<213> ORGANISM: Artificial Sequence
<220> FEATURE:
<223> OTHER INFORMATION: Forward primer

<400> SEQUENCE: 6

```
ggggtaccat gtctcttccc gtctcagtag                                        30
```

<210> SEQ ID NO 7
<211> LENGTH: 30
<212> TYPE: DNA
<213> ORGANISM: Artificial Sequence
<220> FEATURE:
<223> OTHER INFORMATION: Reverse primer

<400> SEQUENCE: 7

```
gctctagatc atattgggat gggatcaatt                                        30
```

DRIMENOL SYNTHASES III

RELATED APPLICATIONS

This application is a national stage application under 35 U.S.C. § 371 filing of International Patent Application PCT/EP2016/076874, filed Nov. 7, 2016, which claims the benefit of International patent application PCT/CN2015/093897 filed Nov. 5, 2015.

TECHNICAL FIELD

The field relates to a method of producing drimenol, said method comprising contacting a polypeptide with farnesyl pyrophosphate (FPP). In particular, said method may be carried out in vitro or in vivo to produce drimenol, a very useful compound in the field of perfumery. Also provided herein is an amino acid sequence of a polypeptide useful in the methods provided herein. A nucleic acid encoding the polypeptide of an embodiment herein and an expression vector containing said nucleic acid are provided herein. A non-human host organism or a cell transformed to be used in the method of producing drimenol is also provided herein.

BACKGROUND

Terpenes are found in most organisms (microorganisms, animals and plants). These compounds are made up of five carbon units called isoprene units and are classified by the number of these units present in their structure. Thus monoterpenes, sesquiterpenes and diterpenes are terpenes containing 10, 15 and 20 carbon atoms, respectively. Sesquiterpenes, for example, are widely found in the plant kingdom. Many sesquiterpene molecules are known for their flavor and fragrance properties and their cosmetic, medicinal and antimicrobial effects. Numerous sesquiterpene hydrocarbons and sesquiterpenoids have been identified.

Biosynthetic production of terpenes involves enzymes called terpene synthases. There is virtually an infinity of sesquiterpene synthases present in the plant kingdom, all using the same substrate (farnesyl pyrophosphate, FPP) but having different product profiles. Genes and cDNAs encoding sesquiterpene synthases have been cloned and the corresponding recombinant enzymes characterized.
Currently the main sources for drimenol are plants naturally containing drimenol and the contents of drimenol in these natural sources are low. Chemical synthesis approaches have been developed but are still complex and not cost-effective.

SUMMARY

Provided herein is a method of producing drimenol comprising:
 i) contacting an acyclic farnesyl diphosphate (FPP) precursor with a polypeptide having drimenol synthase activity and having at least 50%, 55%, 60%, 65%, 70%, 75%, 80%, 85%, 90%, 95%, 96%, 97%, 98% or 99% sequence identity to SEQ ID NO: 2 or comprising SEQ ID NO:2 to produce the drimenol; and
 ii) optionally isolating the drimenol.

Also provided herein is an isolated polypeptide having drimenol synthase activity comprising SEQ ID NO: 2.

Further provided herein is an isolated nucleic acid molecule encoding a polypeptide having drimenol synthase activity and having at least 50%, 55%, 60%, 65%, 70%, 75%, 80%, 85%, 90%, 95%, 96%, 97%, 98% or 99% sequence identity to SEQ ID NO: 2 or comprising SEQ ID NO:2.

Further provided is an isolated nucleic acid molecule encoding a polypeptide provided herein where the molecule has a nucleotide sequence 50%, 55%, 60%, 65%, 70%, 75%, 80%, 85%, 90%, 95%, 96%, 97%, 98% or 99% sequence identity to a nucleotide sequence selected from the group consisting of SEQ ID NO: 1 and SEQ ID NO: 5 or comprising the nucleotide sequence selected from the group consisting of SEQ ID NO: 1 and SEQ ID NO: 5

DETAILED DESCRIPTION

Figure 1:
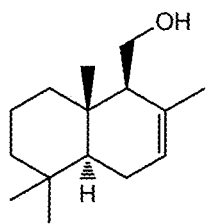
FIG. 1. Structure of (−)-drimenol
FIG. 2. Mass spectrum of authentic (−)-drimenol
FIG. 3. $^{13}$C NMR spectrum of authentic (−)-drimenol.
Figure 2:
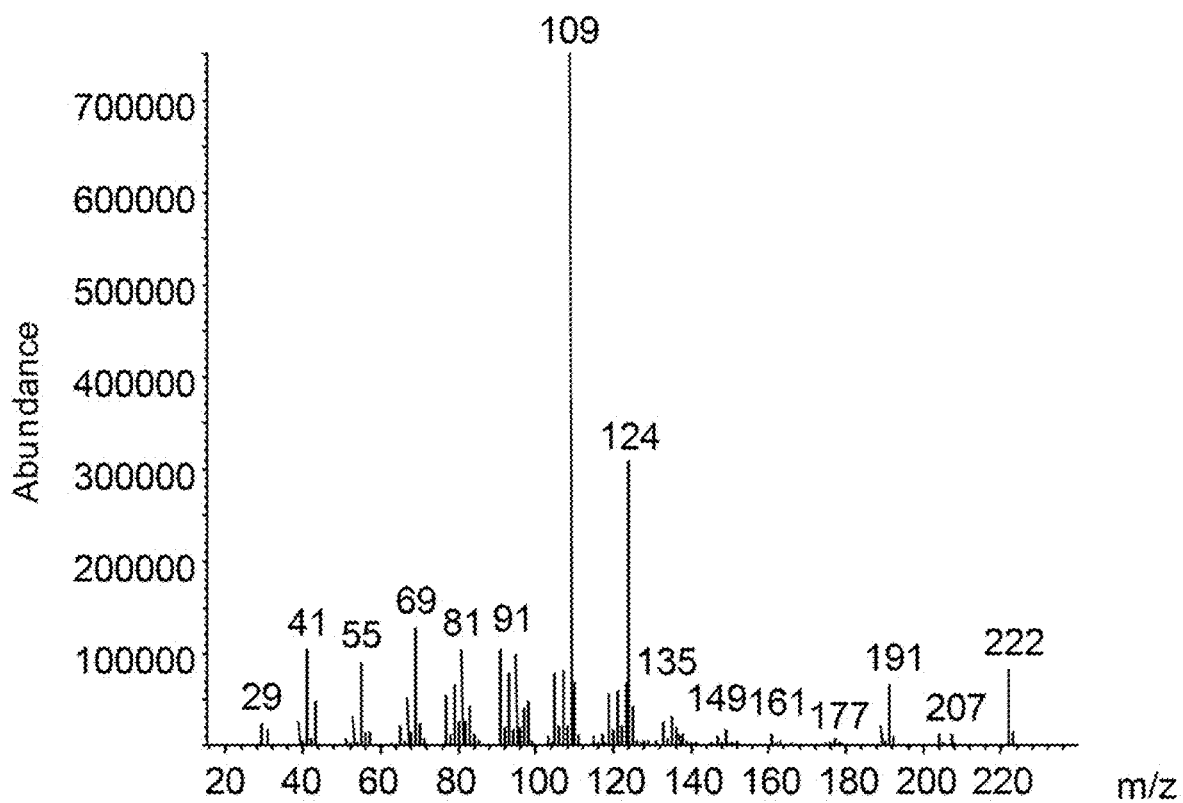
Figure 3:
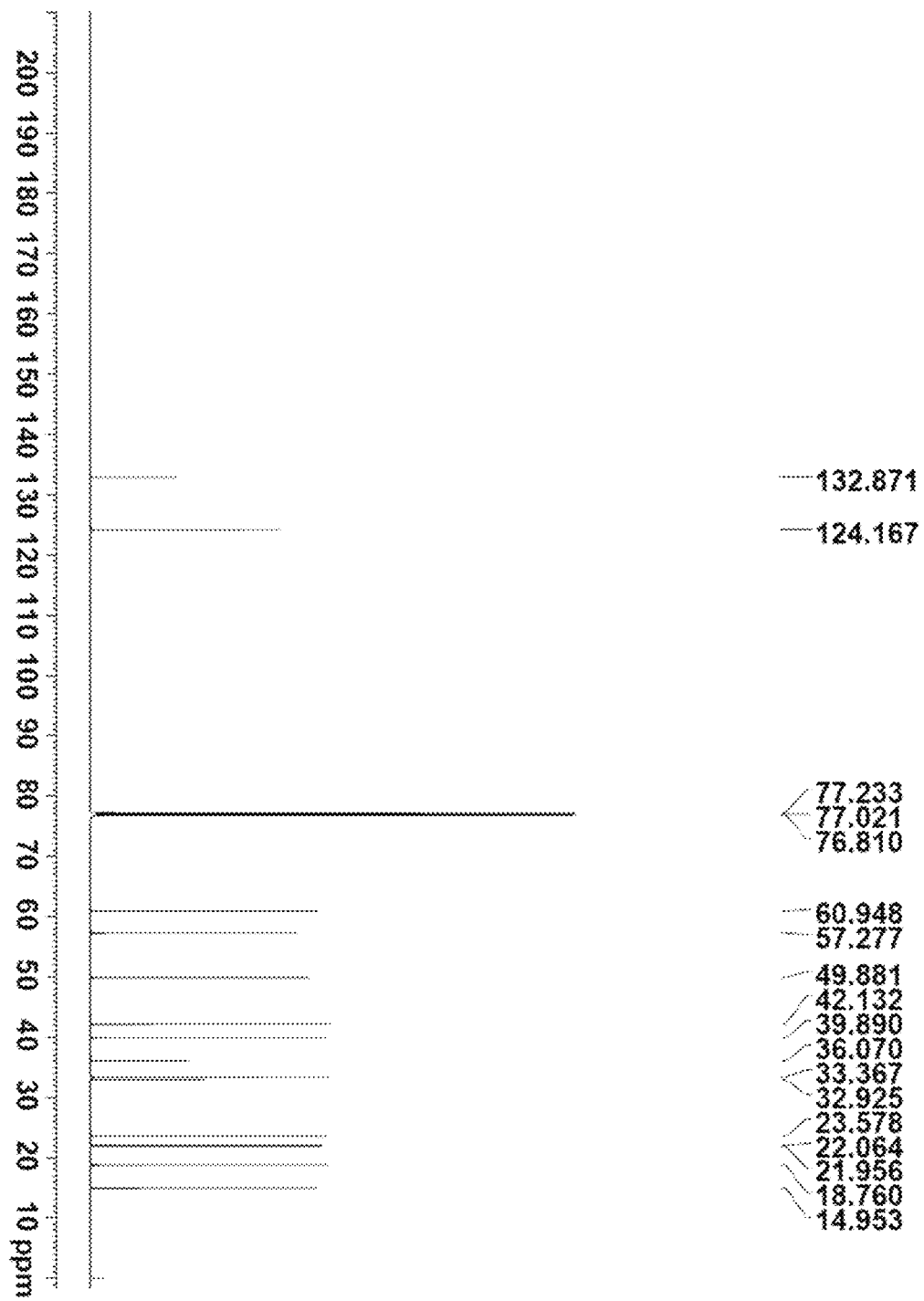
Figure 4:
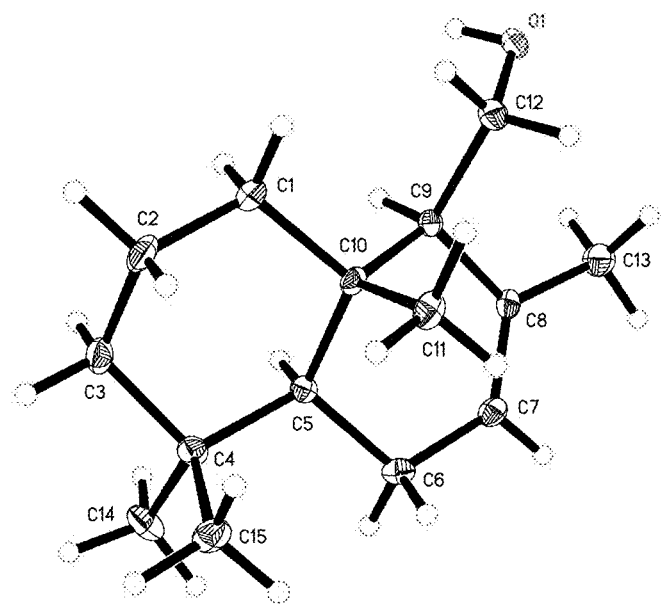
FIG. 4. X-Ray (Cu Kα radiation) structure of authentic (−)-drimenol
FIG. 5. Shows GC/MS extracted ion chromatogram (m/z 109) of *Paeonia anomala* root extract (dichloromethane). The arrow denotes the peak of drimenol.

For the descriptions herein and the appended claims, the use of "or" means "and/or" unless stated otherwise. Similarly, "comprise," "comprises," "comprising", "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of"
In one aspect, provided here is a method of producing drimenol comprising:
 i) contacting an acyclic terpene pyrophosphate, particularly farnesyl diphosphate (FPP)) with a polypeptide having drimenol synthase activity and comprising SEQ ID NO: 2 to produce drimenol; and
 ii) optionally isolating the drimenol.

In one aspect, the drimenol is isolated.
In another aspect provided here, the drimenol is produced with greater than or equal to, 60%, 80%, or 90% or even 95% selectivity.

In one embodiment provided herein is an isolated polypeptide a polypeptide having drimenol synthase activity and having at least 50%, 55%, 60%, 65%, 70%, 75%, 80%, 85%, 90%, 95%, 96%, 97%, 98% or 99% sequence identity to SEQ ID NO: 2.

In one embodiment provided herein is an isolated polypeptide a polypeptide having drimenol synthase activity and having at least 55%, 60%, 65%, 70%, 75%, 80%, 85%, 90%, 95%, 96%, 97%, 98% or 99% sequence identity to SEQ ID NO: 2.

In one embodiment provided herein is an isolated polypeptide a polypeptide having drimenol synthase activity and having at least 60%, 65%, 70%, 75%, 80%, 85%, 90%, 95%, 96%, 97%, 98% or 99% sequence identity to SEQ ID NO: 2.

In one embodiment provided herein is an isolated polypeptide a polypeptide having drimenol synthase activity and having at least 65%, 70%, 75%, 80%, 85%, 90%, 95%, 96%, 97%, 98% or 99% sequence identity to SEQ ID NO: 2.

In one embodiment provided herein is an isolated polypeptide a polypeptide having drimenol synthase activity and having at least 70%, 75%, 80%, 85%, 90%, 95%, 96%, 97%, 98% or 99% sequence identity to SEQ ID NO: 2.

In one embodiment provided herein is an isolated polypeptide a polypeptide having drimenol synthase activity and having at least 75%, 80%, 85%, 90%, 95%, 96%, 97%, 98% or 99% sequence identity to SEQ ID NO: 2.

In one embodiment provided herein is an isolated polypeptide a polypeptide having drimenol synthase activity and having at least 80%, 85%, 90%, 95%, 96%, 97%, 98% or 99% sequence identity to SEQ ID NO: 2.

In one embodiment provided herein is an isolated polypeptide a polypeptide having drimenol synthase activity and having at least 85%, 90%, 95%, 96%, 97%, 98% or 99% sequence identity to SEQ ID NO: 2.

In one embodiment provided herein is an isolated polypeptide a polypeptide having drimenol synthase activity and having at least 90%, 95%, 96%, 97%, 98% or 99% sequence identity to SEQ ID NO: 2.

In one embodiment provided herein is an isolated polypeptide a polypeptide having drimenol synthase activity and having at least 95%, 96%, 97%, 98% or 99% sequence identity to SEQ ID NO: 2.

In one embodiment provided herein is an isolated polypeptide a polypeptide having drimenol synthase activity and having at least 96%, 97%, 98% or 99% sequence identity to SEQ ID NO: 2.

In one embodiment provided herein is an isolated polypeptide a polypeptide having drimenol synthase activity and having at least 97%, 98% or 99% sequence identity to SEQ ID NO: 2.

In one embodiment provided herein is an isolated polypeptide a polypeptide having drimenol synthase activity and having at least 98% or 99% sequence identity to SEQ ID NO: 2.

In one embodiment provided herein is an isolated polypeptide a polypeptide having drimenol synthase activity and having at least 99% sequence identity to SEQ ID NO: 2.

Further provided here is an isolated polypeptide having drimenol activity comprising an amino acid of SEQ ID NO: 2.

Further provided herein is an isolated nucleic acid molecule encoding a polypeptide comprising an amino acid sequence of SEQ ID NO: 2.

Further provided herein a nucleic acid molecule comprising the sequence SEQ ID NO: 1 or SEQ ID NO: 5.

Further provided here is a method as recited in claim 1 comprising the steps of transforming a host cell or non-human organism with a nucleic acid encoding a polypeptide a polypeptide having drimenol synthase activity and having at least 50%, 55%, 60%, 65%, 70%, 75%, 80%, 85%, 90%, 95%, 96%, 97%, 98% or 99% sequence identity to SEQ ID NO: 2 or comprising SEQ ID NO: 2 and culturing the host cell or organism under conditions that allow for the production of the polypeptide.

Further provided is at least one vector comprising the nucleic acid molecules described herein.

Further provided herein is a vector selected from the group of a prokaryotic vector, viral vector and a eukaryotic vector.

Further provided here is a vector that is an expression vector.

As a "drimenol synthase" or as a "polypeptide having a drimenol synthase activity", we mean here a polypeptide capable of catalyzing the synthesis of drimenol, in the form of any of its stereoisomers or a mixture thereof, starting from an acyclic terpene pyrophosphate, particularly FPP. Drimenol may be the only product or may be part of a mixture of sesquiterpenes.

The ability of a polypeptide to catalyze the synthesis of a particular sesquiterpene (for example drimenol) can be simply confirmed by performing the enzyme assay as detailed in Examples 1 to 2.

According to the present invention, polypeptides are also meant to include truncated polypeptides provided that they keep their drimenol synthase activity.

As intended herein below, "a nucleotide sequence obtained by modifying SEQ ID NO: for SEQ ID NO: 5 the complement thereof" encompasses any sequence that has been obtained by changing the sequence of SEQ ID NO: 1 or SEQ ID NO: 5, or of the complement thereof using any method known in the art, for example by introducing any type of mutations such as deletion, insertion or substitution mutations. Examples of such methods are cited in the part of the description relative to the variant polypeptides and the methods to prepare them.

ABBREVIATIONS USED bp base pair
kb kilo base
BSA bovine serum albumin
DNA deoxyribonucleic acid
cDNA complementary DNA
DTT dithiothreitol
FID flame ionization detector
FPP farnesyl pyrophosphate
GC gas chromatograph
IPTG isopropyl-D-thiogalacto-pyranoside
LB lysogeny broth
MS mass spectrometer/mass spectrometry
MVA mevalonic acid
PCR polymerase chain reaction
RMCE recombinase-mediated cassette exchange
3'-/5'-RACE 3' and 5' rapid amplification of cDNA ends
RNA ribonucleic acid
mRNA messenger ribonucleic acid
miRNA micro RNA
siRNA small interfering RNA
rRNA ribosomal RNA
tRNA transfer RNA The term "polypeptide" means an amino acid sequence of consecutively polymerized amino acid residues, for instance, at least 15 residues, at least 30 residues, at least 50 residues. In some embodiments of an embodiment herein, a polypeptide comprises an amino acid sequence that is an enzyme, or a fragment, or a variant thereof.

The term "isolated" polypeptide refers to an amino acid sequence that is removed from its natural environment by any method or combination of methods known in the art and includes recombinant, biochemical and synthetic methods.

The term "protein" refers to an amino acid sequence of any length wherein amino acids are linked by covalent peptide bonds, and includes oligopeptide, peptide, polypeptide and full length protein whether naturally occurring or synthetic.

The terms "drimenol synthase" or "drimenol synthase protein" refer to an enzyme that is capable of converting farnesyl diphosphate (FPP) to drimenol.

The terms "biological function," "function," "biological activity" or "activity" refer to the ability of the drimenol synthase provided herein to catalyze the formation of drimenol from FPP.

The terms "nucleic acid sequence," "nucleic acid," and "polynucleotide" are used interchangeably meaning a sequence of nucleotides. A nucleic acid sequence may be a single-stranded or double-stranded deoxyribonucleotide, or ribonucleotide of any length, and include coding and non-coding sequences of a gene, exons, introns, sense and anti-sense complimentary sequences, genomic DNA, cDNA, miRNA, siRNA, mRNA, rRNA, tRNA, recombinant nucleic acid sequences, isolated and purified naturally occurring DNA and/or RNA sequences, synthetic DNA and RNA sequences, fragments, primers and nucleic acid probes. The skilled artisan is aware that the nucleic acid sequences of RNA are identical to the DNA sequences with the difference of thymine (T) being replaced by uracil (U).

An "isolated nucleic acid" or "isolated nucleic acid sequence" is defined as a nucleic acid or nucleic acid sequence that is in an environment different from that in which the nucleic acid or nucleic acid sequence naturally occurs. The term "naturally-occurring" as used herein as applied to a nucleic acid refers to a nucleic acid that is found in a cell in nature. For example, a nucleic acid sequence that is present in an organism, for instance in the cells of an organism, that can be isolated from a source in nature and which has not been intentionally modified by a human in the laboratory, is naturally occurring.

"Recombinant nucleic acid sequences" are nucleic acid sequences that result from the use of laboratory methods (molecular cloning) to bring together genetic material from more than on source, creating a nucleic acid sequence that does not occur naturally and would not be otherwise found in biological organisms.

"Recombinant DNA technology" refers to molecular biology procedures to prepare a recombinant nucleic acid sequence as described, for instance, in Laboratory Manuals edited by Weigel and Glazebrook, 2002 Cold Spring Harbor Lab Press; and Sambrook et al., 1989 Cold Spring Harbor, N.Y.: Cold Spring Harbor Laboratory Press.

The term "gene" means a DNA sequence comprising a region, which is transcribed into a RNA molecule, e.g., an mRNA in a cell, operably linked to suitable regulatory regions, e.g., a promoter. A gene may thus comprise several operably linked sequences, such as a promoter, a 5' leader sequence comprising, e.g., sequences involved in translation initiation, a coding region of cDNA or genomic DNA, introns, exons, and/or a 3'non-translated sequence comprising, e.g., transcription termination sites.

A "chimeric gene" refers to any gene which is not normally found in nature in a species, in particular, a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more coding sequences or to an antisense, i.e., reverse complement of the sense strand, or inverted repeat sequence (sense and antisense, whereby the RNA transcript forms double stranded RNA upon transcription).

A "3' UTR" or "3' non-translated sequence" (also referred to as "3' untranslated region," or "3'end") refers to the nucleic acid sequence found downstream of the coding sequence of a gene, which comprises for example a transcription termination site and (in most, but not all eukaryotic mRNAs) a polyadenylation signal such as AAUAAA or variants thereof. After termination of transcription, the mRNA transcript may be cleaved downstream of the polyadenylation signal and a poly(A) tail may be added, which is involved in the transport of the mRNA to the site of translation, e.g., cytoplasm.

"Expression of a gene" involves transcription of the gene and translation of the mRNA into a protein. Overexpression refers to the production of the gene product as measured by levels of mRNA, polypeptide and/or enzyme activity in transgenic cells or organisms that exceeds levels of production in non-transformed cells or organisms of a similar genetic background.

"Expression vector" as used herein means a nucleic acid molecule engineered using molecular biology methods and recombinant DNA technology for delivery of foreign or exogenous DNA into a host cell. The expression vector typically includes sequences required for proper transcription of the nucleotide sequence. The coding region usually codes for a protein of interest but may also code for an RNA, e.g., an antisense RNA, siRNA and the like.

An "expression vector" as used herein includes any linear or circular recombinant vector including but not limited to viral vectors, bacteriophages and plasmids. The skilled person is capable of selecting a suitable vector according to the expression system. In one embodiment, the expression vector includes the nucleic acid of an embodiment herein operably linked to at least one regulatory sequence, which controls transcription, translation, initiation and termination, such as a transcriptional promoter, operator or enhancer, or an mRNA ribosomal binding site and, optionally, including at least one selection marker. Nucleotide sequences are "operably linked" when the regulatory sequence functionally relates to the nucleic acid of an embodiment herein.

"Regulatory sequence" refers to a nucleic acid sequence that determines expression level of the nucleic acid sequences of an embodiment herein and is capable of regulating the rate of transcription of the nucleic acid sequence operably linked to the regulatory sequence. Regulatory sequences comprise promoters, enhancers, transcription factors, promoter elements and the like.

"Promoter" refers to a nucleic acid sequence that controls the expression of a coding sequence by providing a binding site for RNA polymerase and other factors required for proper transcription including without limitation transcription factor binding sites, repressor and activator protein binding sites. The meaning of the term promoter also includes the term "promoter regulatory sequence". Promoter regulatory sequences may include upstream and downstream elements that may influences transcription, RNA processing or stability of the associated coding nucleic acid sequence. Promoters include naturally-derived and synthetic sequences. The coding nucleic acid sequences is usually located downstream of the promoter with respect to the direction of the transcription starting at the transcription initiation site.

The term "constitutive promoter" refers to an unregulated promoter that allows for continual transcription of the nucleic acid sequence it is operably linked to.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous. The nucleotide sequence associated with the promoter sequence may be of homologous or heterologous origin with respect to the plant to be transformed. The sequence also may be entirely or partially synthetic. Regardless of the origin, the nucleic acid sequence associated with the promoter sequence will be expressed or silenced in accordance with promoter properties to which it is linked after binding to the polypeptide of an embodiment herein. The associated nucleic acid may code for a protein that is desired to be expressed or suppressed throughout the organism at all times or, alternatively, at a specific time or in specific tissues, cells, or cell compartment. Such nucleotide sequences particularly encode proteins conferring desirable phenotypic traits to the host cells or organism altered or transformed therewith. More particularly, the associated nucleotide sequence leads to the production of drimenol in the organism. Particularly, the nucleotide sequence encodes drimenol synthase.

"Target peptide" refers to an amino acid sequence which targets a protein, or polypeptide to intracellular organelles, i.e., mitochondria, or plastids, or to the extracellular space (secretion signal peptide). A nucleic acid sequence encoding a target peptide may be fused to the nucleic acid sequence encoding the amino terminal end, e.g., N-terminal end, of the protein or polypeptide, or may be used to replace a native targeting polypeptide.

The term "primer" refers to a short nucleic acid sequence that is hybridized to a template nucleic acid sequence and is used for polymerization of a nucleic acid sequence complementary to the template.

As used herein, the term "host cell" or "transformed cell" refers to a cell (or organism) altered to harbor at least one nucleic acid molecule, for instance, a recombinant gene encoding a desired protein or nucleic acid sequence which upon transcription yields a drimenol synthase protein useful to produce drimenol. The host cell is particularly a bacterial cell, a fungal cell or a plant cell. The host cell may contain a recombinant gene according to the present invention which has been integrated into the nuclear or organelle genomes of the host cell. Alternatively, the host may contain the recombinant gene extra-chromosomally. Homologous sequences include orthologous or paralogous sequences. Methods of identifying orthologs or paralogs including phylogenetic methods, sequence similarity and hybridization methods are known in the art and are described herein.

Paralogs result from gene duplication that gives rise to two or more genes with similar sequences and similar functions. Paralogs typically cluster together and are formed by duplications of genes within related plant species. Paralogs are found in groups of similar genes using pair-wise Blast analysis or during phylogenetic analysis of gene families using programs such as CLUSTAL. In paralogs, consensus sequences can be identified characteristic to sequences within related genes and having similar functions of the genes.

Orthologs, or orthologous sequences, are sequences similar to each other because they are found in species that descended from a common ancestor. For instance, plant species that have common ancestors are known to contain many enzymes that have similar sequences and functions. The skilled artisan can identify orthologous sequences and predict the functions of the orthologs, for example, by constructing a polygenic tree for a gene family of one species using CLUSTAL or BLAST programs. A method for identifying or confirming similar functions among homologous sequences is by comparing of the transcript profiles in plants overexpressing or lacking (in knockouts/knockdowns) related polypeptides. The skilled person will understand that genes having similar transcript profiles, with greater than 50% regulated transcripts in common, or with greater than 70% regulated transcripts in common, or greater than 90% regulated transcripts in common will have similar functions. Homologs, paralogs, orthologs and any other variants of the sequences herein are expected to function in a similar manner by making plants producing drimenol synthase proteins.

An embodiment provided herein provides amino acid sequences of drimenol synthase proteins including orthologs and paralogs as well as methods for identifying and isolating orthologs and paralogs of the drimenol synthases in other organisms. Particularly, so identified orthologs and paralogs of the drimenol synthase retain drimenol synthase activity and are capable of producing drimenol starting from FPP precursors.

The term "selectable marker" refers to any gene which upon expression may be used to select a cell or cells that include the selectable marker. Examples of selectable markers are described below. The skilled artisan will know that different antibiotic, fungicide, auxotrophic or herbicide selectable markers are applicable to different target species.

"Drimenol" for purposes of this application refers to (−)-drimenol (CAS: 468-68-8).

The term "organism" refers to any non-human multicellular or unicellular organisms such as a plant, or a microorganism. Particularly, a micro-organism is a bacterium, a yeast, an algae or a fungus.

The term "plant" is used interchangeably to include plant cells including plant protoplasts, plant tissues, plant cell tissue cultures giving rise to regenerated plants, or parts of plants, or plant organs such as roots, stems, leaves, flowers, pollen, ovules, embryos, fruits and the like. Any plant can be used to carry out the methods of an embodiment herein.

The polypeptide to be contacted with an acyclic pyrophosphate, e.g. FPP, in vitro can be obtained by extraction from any organism expressing it, using standard protein or enzyme extraction technologies. If the host organism is an unicellular organism or cell releasing the polypeptide of an embodiment herein into the culture medium, the polypeptide may simply be collected from the culture medium, for example by centrifugation, optionally followed by washing steps and re-suspension in suitable buffer solutions. If the organism or cell accumulates the polypeptide within its cells, the polypeptide may be obtained by disruption or lysis of the cells and further extraction of the polypeptide from the cell lysate.

The polypeptide having a drimenol synthase activity, either in an isolated form or together with other proteins, for example in a crude protein extract obtained from cultured cells or microorganisms, may then be suspended in a buffer solution at optimal pH. If adequate, salts, DTT, inorganic cations and other kinds of enzymatic co-factors, may be added in order to optimize enzyme activity. The precursor FPP is added to the polypeptide suspension, which is then incubated at optimal temperature, for example between 15 and 40° C., particularly between 25 and 35° C., more particularly at 30° C. After incubation, the drimenol produced may be isolated from the incubated solution by standard isolation procedures, such as solvent extraction and distillation, optionally after removal of polypeptides from the solution.

According to another particularly embodiment, the method of any of the above-described embodiments is carried out in vivo. In this case, step a) comprises cultivating a non-human host organism or cell capable of producing FPP and transformed to express at least one polypeptide comprising an amino acid comprising SEQ ID NO: 2 and having a drimenol synthase activity, under conditions conducive to the production of drimenol.

According to a more particular embodiment, the method further comprises, prior to step a), transforming a non-human organism or cell capable of producing FPP with at least one nucleic acid encoding a polypeptide comprising an amino acid comprising SEQ ID NO: 2 and having a drimenol synthase activity, so that said organism expresses said polypeptide.

These embodiments of an embodiment herein are particularly advantageous since it is possible to carry out the method in vivo without previously isolating the polypeptide. The reaction occurs directly within the organism or cell transformed to express said polypeptide.

According to a more particular embodiment at least one nucleic acid used in any of the above embodiments comprises a nucleotide sequence that has been obtained by modifying SEQ ID NO: 1 or SEQ ID NO: 5 or the complement thereof. According to another embodiment, the at least one nucleic acid is isolated from a plant of the Paeoniaceae family, particularly from *Paeonia anomala*. The organism or cell is meant to "express" a polypeptide, provided that the organism or cell is transformed to harbor a nucleic acid encoding said polypeptide, this nucleic acid is transcribed to mRNA and the polypeptide is found in the host organism or cell. The term "express" encompasses "heterologously express" and "over-express", the latter referring to levels of mRNA, polypeptide and/or enzyme activity over and above what is measured in a non-transformed organism or cell. A more detailed description of suitable methods to transform a non-human host organism or cell will be described later on in the part of the specification that is dedicated to such transformed non-human host organisms or cells as specific objects provided herein and in the examples.

A particular organism or cell is meant to be "capable of producing FPP" when it produces FPP naturally or when it does not produce FPP naturally but is transformed to produce FPP, either prior to the transformation with a nucleic acid as described herein or together with said nucleic acid. Organisms or cells transformed to produce a higher amount of FPP than the naturally occurring organism or cell are also encompassed by the "organisms or cells capable of producing FPP". Methods to transform organisms, for example microorganisms, so that they produce FPP are already known in the art.

To carry out an embodiment herein in vivo, the host organism or cell is cultivated under conditions conducive to the production of drimenol. Accordingly, if the host is a transgenic plant, optimal growth conditions are provided, such as optimal light, water and nutrient conditions, for example. If the host is a unicellular organism, conditions conducive to the production of drimenol may comprise addition of suitable cofactors to the culture medium of the host. In addition, a culture medium may be selected, so as to maximize drimenol synthesis. Optimal culture conditions are described in a more detailed manner in the following Examples.

Non-human host organisms suitable to carry out the method of an embodiment herein in vivo may be any non-human multicellular or unicellular organisms. In a particular embodiment, the non-human host organism used to carry out an embodiment herein in vivo is a plant, a prokaryote or a fungus. Any plant, prokaryote or fungus can be used. Particularly useful plants are those that naturally produce high amounts of terpenes. In a more particular embodiment the non-human host organism used to carry out the method of an embodiment herein in vivo is a microorganism. Any microorganism can be used but according to an even more particular embodiment said microorganism is a bacteria or yeast. Most particularly, said bacteria is *Escherichia coli* and said yeast is *Saccharomyces cerevisiae*.

Some of these organisms do not produce FPP naturally. To be suitable to carry out the method of an embodiment herein, these organisms have to be transformed to produce said precursor. They can be so transformed either before the modification with the nucleic acid described according to any of the above embodiments or simultaneously, as explained above.

Isolated higher eukaryotic cells can also be used, instead of complete organisms, as hosts to carry out the method of an embodiment herein in vivo. Suitable eukaryotic cells may be any non-human cell, but are particularly plant or fungal cells.

In another particular embodiment, the polypeptide comprises SEQ ID NO: 2.

According to another particular embodiment, the at least one polypeptide having a drimenol synthase activity used in any of the above-described embodiments or encoded by the nucleic acid used in any of the above-described embodiments comprises an amino acid sequence that is a variant of SEQ ID NO: 2, obtained by genetic engineering, provided that said variant keeps its Drimenol synthase activity, as defined above and has the required percentage of identity to SEQ ID NO: 2. In other terms, said polypeptide particularly comprises an amino acid sequence encoded by a nucleotide sequence that has been obtained by modifying SEQ ID NO: 1 or SEQ ID NO: 5 or the complement thereof. According to a more particular embodiment, the at least one polypeptide having a drimenol synthase activity used in any of the above-described embodiments or encoded by the nucleic acid used in any of the above-described embodiments consists of an amino acid sequence that is a variant to of SEQ ID NO: 2, obtained by genetic engineering, i.e. an amino acid sequence encoded by a nucleotide sequence that has been obtained by modifying SEQ ID NO: 1 or SEQ ID NO: 5 or the complement thereof.

According to another particular embodiment, the at least one polypeptide having a Drimenol synthase activity used in any of the above-described embodiments or encoded by the nucleic acid used in any of the above-described embodiments is a variant of SEQ ID NO: 2 that can be found naturally in other organisms, such as other plant species, provided that it keeps its Drimenol synthase activity. As used herein, the polypeptide is intended as a polypeptide or peptide fragment that encompasses the amino acid sequences identified herein, as well as truncated or variant polypeptides, provided that they keep their drimenol synthase activity as defined above and that they share at least the defined percentage of identity with the corresponding fragment of SEQ ID NO: 2.

Examples of variant polypeptides are naturally occurring proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides of an embodiment herein. Polypeptides encoded by a nucleic acid obtained by natural or artificial mutation of a nucleic acid of an embodiment herein, as described thereafter, are also encompassed by an embodiment herein.

Polypeptide variants resulting from a fusion of additional peptide sequences at the amino and carboxyl terminal ends can also be used in the methods of an embodiment herein. In particular such a fusion can enhance expression of the polypeptides, be useful in the purification of the protein or improve the enzymatic activity of the polypeptide in a desired environment or expression system. Such additional peptide sequences may be signal peptides, for example. Accordingly, the present invention encompasses methods using variant polypeptides, such as those obtained by fusion with other oligo- or polypeptides and/or those which are linked to signal peptides. Polypeptides resulting from a fusion with another functional protein, such as another protein from the terpene biosynthesis pathway, can also be advantageously be used in the methods of an embodiment herein.

According to another embodiment, the at least one polypeptide having a drimenol synthase activity used in any of the above-described embodiments or encoded by the nucleic acid used in any of the above-described embodiments is isolated from a plant of the Paeoniaceae family, particularly from *Paeonia anomala*. An important tool to carry out the method of an embodiment herein is the polypeptide itself. A polypeptide having a drimenol synthase activity and comprising an amino acid sequence of SEQ ID NO: 2 is therefore provided herein.

According to a particular embodiment, the polypeptide is capable of producing a mixture of sesquiterpenes wherein drimenol represents at least 20%, particularly at least 30%, particularly at least 35%, particularly at least 90%, particularly at least 95%, more particularly at least 98% of the sesquiterpenes produced. In another aspect provided here, the drimenol is produced with greater than or equal to 95%, more particularly 98% selectivity.

According to a particular embodiment, the polypeptide comprises an amino acid sequence of SEQ ID NO: 2.

According to another particular embodiment, the polypeptide consists of SEQ ID NO: 2.

The at least one polypeptide comprises an amino acid sequence that is a variant of SEQ ID NO: 2, either obtained by genetic engineering or found naturally in *Paeonia* plants or in other plant species. In other terms, when the variant polypeptide is obtained by genetic engineering, said polypeptide comprises an amino acid sequence encoded by a nucleotide sequence that has been obtained by modifying SEQ ID NO: 5 or the complement thereof. According to a more particular embodiment, the at least one polypeptide having a drimenol synthase activity consists of an amino acid sequence that is a variant of SEQ ID NO: 2 obtained by genetic engineering, i.e. an amino acid sequence encoded by a nucleotide sequence that has been obtained by modifying SEQ ID NO: 5.

According to another embodiment, the polypeptide is isolated from a plant of the Paeoniaceae family, particularly from *Paeonia anomala*. As used herein, the polypeptide is intended as a polypeptide or peptide fragment that encompasses the amino acid sequence identified herein, as well as truncated or variant polypeptides, provided that they keep their activity as defined above and that they share at least the defined percentage of identity with the corresponding fragment of SEQ ID NO: 2.

As mentioned above, the nucleic acid encoding the polypeptide of an embodiment herein is a useful tool to modify non-human host organisms or cells intended to be used when the method is carried out in vivo.

A nucleic acid encoding a polypeptide according to any of the above-described embodiments is therefore also provided herein.

According to a more particular embodiment, the nucleic acid comprises SEQ ID NO: 1 or SEQ ID NO: 5 or the complement thereof.

According to another particular embodiment, the nucleic acid consists of a nucleotide sequence SEQ ID NO: 5 or the complement thereof.

The nucleic acid of an embodiment herein can be defined as including deoxyribonucleotide or ribonucleotide polymers in either single- or double-stranded form (DNA and/or RNA). The terms "nucleotide sequence" should also be understood as comprising a polynucleotide molecule or an oligonucleotide molecule in the form of a separate fragment or as a component of a larger nucleic acid. Nucleic acids of an embodiment herein also encompass certain isolated nucleotide sequences including those that are substantially free from contaminating endogenous material. The nucleic acid of an embodiment herein may be truncated, provided that it encodes a polypeptide encompassed by the present invention, as described above.

In one embodiment, the nucleic acid of an embodiment herein can be either present naturally in plants of the *Paeonia* species or other species, or be obtained by modifying SEQ ID NO: 1 or SEQ ID NO: 5 or the complement thereof.

The nucleic acids comprising a sequence obtained by mutation of SEQ ID NO: 1 or SEQ ID NO: 5 or the complement thereof are encompassed by an embodiment herein, provided that the sequences they comprise share at least the defined sequence of SEQ ID NO: 1 or SEQ ID NO: 5 or the complement thereof and provided that they encode a polypeptide having a drimenol synthase activity, as defined in any of the above embodiments. Mutations may be any kind of mutations of these nucleic acids, such as point mutations, deletion mutations, insertion mutations and/or frame shift mutations. A variant nucleic acid may be prepared in order to adapt its nucleotide sequence to a specific expression system. For example, bacterial expression systems are known to more efficiently express polypeptides if amino acids are encoded by particular codons.

Due to the degeneracy of the genetic code, more than one codon may encode the same amino acid sequence, multiple nucleic acid sequences can code for the same protein or polypeptide, all these DNA sequences being encompassed by an embodiment herein. Where appropriate, the nucleic acid sequences encoding the drimenol synthase may be optimized for increased expression in the host cell. For example, nucleotides of an embodiment herein may be synthesized using codons particular by a host for improved expression.

Another important tool for transforming host organisms or cells suitable to carry out the method of an embodiment herein in vivo is an expression vector comprising a nucleic acid according to any embodiment of an embodiment herein. Such a vector is therefore also provided herein.

The expression vectors provided herein may be used in the methods for preparing a genetically transformed host organism and/or cell, in host organisms and/or cells harboring the nucleic acids of an embodiment herein and in the methods for making polypeptides having a drimenol synthase activity, as disclosed further below.

Recombinant non-human host organisms and cells transformed to harbor at least one nucleic acid of an embodiment herein so that it heterologously expresses or over-expresses at least one polypeptide of an embodiment herein are also very useful tools to carry out the method of an embodiment herein. Such non-human host organisms and cells are therefore provided herein.

A nucleic acid according to any of the above-described embodiments can be used to transform the non-human host organisms and cells and the expressed polypeptide can be any of the above-described polypeptides.

Non-human host organisms of an embodiment herein may be any non-human multicellular or unicellular organisms. In a particular embodiment, the non-human host organism is a plant, a prokaryote or a fungus. Any plant, prokaryote or fungus is suitable to be transformed according to the methods described herein. Particularly useful plants are those that naturally produce high amounts of terpenes.

In a more particular embodiment the non-human host organism is a microorganism. Any microorganism is suitable as a non-human host, but according to an even more particular embodiment said microorganism is a bacterium or yeast. Most particularly, said bacterium is *E. coli* and said yeast is *Saccharomyces cerevisiae*.

Isolated higher eukaryotic cells can also be transformed, instead of complete organisms. As higher eukaryotic cells, we mean here any non-human eukaryotic cell except yeast cells. Particular higher eukaryotic cells are plant cells or fungal cells.

A variant may also differ from the polypeptide of an embodiment herein by attachment of modifying groups which are covalently or non-covalently linked to the polypeptide backbone. The variant also includes a polypeptide which differs from the polypeptide provided herein by introduced N-linked or O-linked glycosylation sites, and/or an addition of cysteine residues. The skilled artisan will recognize how to modify an amino acid sequence and preserve biological activity. The functionality or activity of any drimenol synthase protein, variant or fragment, may be determined using various methods. For example, transient or stable overexpression in plant, bacterial or yeast cells can be used to test whether the protein has activity, i.e., produces drimenol from FPP precursors. Drimenol synthase activity may be assessed in a microbial expression system, such as the assay described in Example 2 herein on the production of drimenol, indicating functionality. A variant or derivative of a drimenol synthase polypeptide of an embodiment herein retains an ability to produce drimenol from FPP precursors. Amino acid sequence variants of the drimenol synthases provided herein may have additional desirable biological functions including, e.g., altered substrate utilization, reaction kinetics, product distribution or other alterations.

An embodiment herein provides polypeptides of an embodiment herein to be used in a method to produce drimenol contacting an FPP precursor with the polypeptides of an embodiment herein either in vitro or in vivo.

Provided herein is also an isolated, recombinant or synthetic polynucleotide encoding a polypeptide or variant polypeptide provided herein. An embodiment of an embodiment herein provides an isolated, recombinant or synthetic nucleic acid sequence of SEQ ID NO: 1 or SEQ ID NO: 5 encoding for a drimenol synthase having the amino acid sequence of SEQ ID NO: 2, or fragments thereof that catalyze production of drimenol in a cell from a FPP precursor. Provided herein are also cDNA, genomic DNA and RNA sequences. Any nucleic acid sequence encoding the drimenol synthase or variants thereof is referred herein as a drimenol synthase encoding sequence.

According to a particular embodiment, the nucleic acid of SEQ ID NO: 1 or SEQ ID NO: 5 is the coding sequence of a drimenol synthase gene encoding the drimenol synthase obtained as described in the Examples.

A fragment of a polynucleotide of SEQ ID NO: 1 or SEQ ID NO: 5 refers to contiguous nucleotides that is particularly at least 15 bp, at least 30 bp, at least 40 bp, at least 50 bp and/or at least 60 bp in length of the polynucleotide of an embodiment herein. Particularly the fragment of a polynucleotide comprises at least 25, more particularly at least 50, more particularly at least 75, more particularly at least 100, more particularly at least 150, more particularly at least 200, more particularly at least 300, more particularly at least 400, more particularly at least 500, more particularly at least 600, more particularly at least 700, more particularly at least 800, more particularly at least 900, more particularly at least 1000 contiguous nucleotides of the polynucleotide of an embodiment herein. Without being limited, the fragment of the polynucleotides herein may be used as a PCR primer, and/or as a probe, or for anti-sense gene silencing or RNAi.

It is clear to the person skilled in the art that genes, including the polynucleotides of an embodiment herein, can be cloned on basis of the available nucleotide sequence information, such as found in the attached sequence listing, by methods known in the art. These include e.g. the design of DNA primers representing the flanking sequences of such gene of which one is generated in sense orientations and which initiates synthesis of the sense strand and the other is created in reverse complementary fashion and generates the antisense strand. Thermo stable DNA polymerases such as those used in polymerase chain reaction are commonly used to carry out such experiments. Alternatively, DNA sequences representing genes can be chemically synthesized and subsequently introduced in DNA vector molecules that can be multiplied by e.g. compatible bacteria such as e.g. *E. coli*.

In a related embodiment provided herein, PCR primers and/or probes for detecting nucleic acid sequences encoding a drimenol synthase are provided. The skilled artisan will be aware of methods to synthesize degenerate or specific PCR primer pairs to amplify a nucleic acid sequence encoding the drimenol synthase or fragments thereof, based on SEQ ID NO: 1 or SEQ ID NO: 5. A detection kit for nucleic acid sequences encoding the drimenol synthase may include primers and/or probes specific for nucleic acid sequences encoding the drimenol synthase, and an associated protocol to use the primers and/or probes to detect nucleic acid sequences encoding the drimenol synthase in a sample. Such detection kits may be used to determine whether a plant has been modified, i.e., transformed with a sequence encoding the drimenol synthase.

The nucleic acid sequences obtained by mutations of SEQ ID NO: 1 or SEQ ID NO: 5 can be routinely made and are also within embodiments provided herein. It is clear to the skilled artisan that mutations, deletions, insertions, and/or substitutions of one or more nucleotides can be introduced into the DNA sequence of SEQ ID NO: 5. Generally, a mutation is a change in the DNA sequence of a gene that can alter the amino acid sequence of the polypeptide produced.

To test a function of variant DNA sequences according to an embodiment herein, the sequence of interest is operably linked to a selectable or screenable marker gene and expression of the reporter gene is tested in transient expression assays with protoplasts or in stably transformed plants. The skilled artisan will recognize that DNA sequences capable of driving expression are built as modules. Accordingly, expression levels from shorter DNA fragments may be different than the one from the longest fragment and may be different from each other. Provided herein are also functional equivalents of the nucleic acid sequence coding the drimenol synthase proteins provided herein, i.e., nucleotide sequences that hybridize under stringent conditions to the nucleic acid sequence of SEQ ID NO: 1 or SEQ ID NO: 5.

The skilled artisan will be aware of methods to identify homologous sequences in other organisms and methods (identified in the Definition section herein) to determine the percentage of sequence identity between homologous sequences. Such newly identified DNA molecules then can be sequenced and the sequence can be compared with the nucleic acid sequence of SEQ ID NO: 1 or SEQ ID NO: 5.

A related embodiment provided herein provides a nucleic acid sequence which is complementary to the nucleic acid sequence according to SEQ ID NO: 1 or SEQ ID NO: 5 such as inhibitory RNAs, or nucleic acid sequence which hybridizes under stringent conditions to at least part of the nucleotide sequence according to SEQ ID NO: 1 or SEQ ID NO: 5. An alternative embodiment of an embodiment herein provides a method to alter gene expression in a host cell. For instance, the polynucleotide of an embodiment herein may be enhanced or overexpressed or induced in certain contexts (e.g. following insect bites or stings or upon exposure to a certain temperature) in a host cell or host organism.

Alteration of expression of a polynucleotide provided herein also results in "ectopic expression" which is a different expression pattern in an altered and in a control or wild-type organism. Alteration of expression occurs from interactions of polypeptide of an embodiment herein with exogenous or endogenous modulators, or as a result of chemical modification of the polypeptide. The term also refers to an altered expression pattern of the polynucleotide of an embodiment herein which is altered below the detection level or completely suppressed activity.

In one embodiment, several drimenol synthases encoding nucleic acid sequences are co-expressed in a single host, particularly under control of different promoters. Alternatively, several drimenol synthase proteins encoding nucleic acid sequences can be present on a single transformation vector or be co-transformed at the same time using separate vectors and selecting transformants comprising both chimeric genes. Similarly, one or more drimenol synthase encoding genes may be expressed in a single plant together with other chimeric genes, for example encoding other proteins which enhance insect pest resistance, or others.

The nucleic acid sequences of an embodiment herein encoding drimenol synthase proteins can be inserted in expression vectors and/or be contained in chimeric genes inserted in expression vectors, to produce drimenol synthase proteins in a host cell or host organism. The vectors for inserting transgenes into the genome of host cells are well known in the art and include plasmids, viruses, cosmids and artificial chromosomes. Binary or co-integration vectors into which a chimeric gene is inserted are also used for transforming host cells.

An embodiment provided herein provides recombinant expression vectors comprising a nucleic acid sequence of a drimenol synthase gene, or a chimeric gene comprising a nucleic acid sequence of a drimenol synthase gene, operably linked to associated nucleic acid sequences such as, for instance, promoter sequences. For example, a chimeric gene comprising a nucleic acid sequence of SEQ ID NO: 1 or SEQ ID NO: 5 or may be operably linked to a promoter sequence suitable for expression in plant cells, bacterial cells or fungal cells, optionally linked to a 3' non-translated nucleic acid sequence.

Alternatively, the promoter sequence may already be present in a vector so that the nucleic acid sequence which is to be transcribed is inserted into the vector downstream of the promoter sequence. Vectors are typically engineered to have an origin of replication, a multiple cloning site, and a selectable marker.

The following examples are illustrative only and are not intended to limit the scope of the claims an embodiments described herein.

EXAMPLES

Example 1

*Paeonia anomala* Plant Material Sourcing and Root Transcriptome Sequencing

Figure 5:
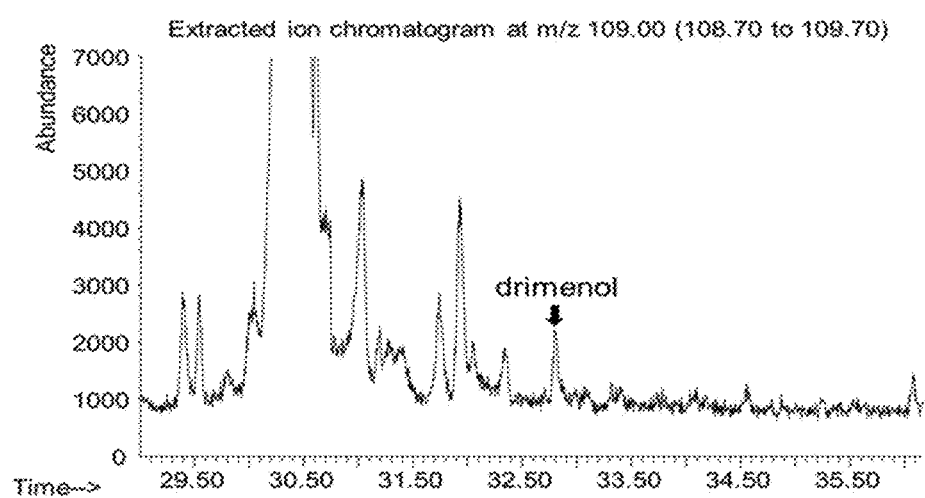

*Paeonia anomala* plant material was obtained from Datong in Qinghai, China. To establish if *Paeonia anomala* contained drimenol, the roots were collected, dried in the shade and extracted with dichloromethane. The extract was analyzed by GC-MS, the parameters of GC-MS analysis were described as below: An Agilent 6890 series GC system equipped with a DB1-ms column 30 m×0.25 mm×0.25 μm film thickness, P/N 122-0132 (J&W scientific Inc, Folsom, Calif.) and coupled with a 5975 series mass spectrometer was used. The carrier gas was helium at a constant flow of 0.7 mL/min. Injection was in split (1:5) mode with the injector temperature set at 250° C. The oven temperature was programmed from 50° C. (5 min hold) to 300° C. at 5° C./min, then to 340° C. at 50° C./min and held for 3 min. Identification of products was based on comparison to data recorded from an authentic standard. The roots of *Paeonia anomala* contained a small amount of drimenol (FIG. 5).

Fresh roots of *Paeonia anomala* were used for transcriptome analysis. Total RNA was extracted using the Column Plant RNA out (TIANDZ, China). This total RNA was processed using the Illumina Total RNA-Seq technique and sequenced on Illumina MiSeq sequencer. A total of 9 million of paired-end reads of 2×251 bp were generated. The reads were assembled using the Trinity (http://trinitymaseq.sf.net/) software. 26457unigenes with an average size of 1109 bp were obtained. The unigenes were annotated by NCBI Blast (http://www.ncbi.nlm.nih.gov/) as well as InterProScan software (http://www.ebi.ac.uk/Tools/pfa/iprscan/). This approach provided the sequences for 7 new putative sesquiterpene synthases including PaTPS1. The enzymatic activity of PaTPS1 was evaluated as described in the following examples.

Example 2

Functional Expression and Characterization of PaTPS1 from *P. anomala*

The total RNA extracted by Column Plant RNA out kit was first reverse transcribed into cDNA using the SuperScriptIII First-Strand Synthesis kit (Invitrogen, Shanghai, China). And then the product was used as the template, forward primer (5'-GGGGTACCATGTCTCTTC-CCGTCTCAGTAG-3') and reverse primer (5'-GCTCTA-GATCATATTGGGATGGGATCAATT-3') were used to amplify the gene from the cDNA library of *P. anomala*, and restriction site of KpnI was added to the 5' end of PaTPS1 while XbaI was added to the 3' end. PaTPS1 was then sub-cloned into a modified binary vector pCAMBIA2300-35S-OCS-35S-GgFPSopt to form pCAMBIA2300-35S-OCS-35S-GgFPSopt-PaTPS1 (pGgFPS-PaTPS1 in short).

pCAMBIA2300-35S-OCS-35S-GgFPSopt is an engineered vector based on the commercial plasmid pCAMBIA2300 (Cambia). Cauliflower Mosaic Virus promoter (CaMV35S) was inserted between the EcoRI and KpnI restriction sites, the octopine synthase (OCS) terminator was inserted between the PstI and HindIII, and the kanamycin resistance gene inside the right and the left borders of transfer DNA (T-Border) of pCAMBIA2300 plasmid was replaced by the codon optimized *Gallus gallus* farnesyl-diphosphate synthase (GgFPS) using XhoI restriction enzyme followed by direction confirmation. The binary vector pCAMBIA2300-35S-OCS-35S-GgFPSopt was thus formed to produce the precursor of sesquiterpene synthase, Farnesylpyrophosphate (FPP).

1 micro gram of pGgFPS-PaTPS1 in short plasmid was transformed into agrobacteria EHA105. Transformed cells were selected on kanamycin (50 μg/mL) and rifampicin (25 μg/mL) LB-agarose plates at 28° C. for 2 days. Single colony was inoculated into 25 mL LB with the same antibiotics and incubated at 28° C. in a shaker with 200 rpm speed overnight. When the OD600 reached 1.0, the culture was centrifuged at 5000 rpm for 10 min at room temperature. The precipitates were re-suspended with 20 mL MgSO$_4$ (10 mM). The suspension was then centrifuged again and the precipitates were re-suspended with 5 mL Acetosyringone (AS) solution (765 μM), then the OD600 was adjusted to 1.0 with AS solution.

The agrobacteria strain transformed with the tomato bushy stunt virus p19 which could suppress gene silencing was mixed with the strain transformed with pGgFPS-PaTPS1 with volume ratio 1:1. The mixture was infiltrated into intercellular space from the abaxial side of 4-week old tobacco leaves grown at 28° C. with 12 hour light/12 hour dark photoperiod. 3 days later, the infected leaves were fed with mevalonate (25 mM). After 8 hours the leaf samples were harvested and about 100-300 mg of the leaf was weighed into 10 mL Eppendorf tube with 2 beads and frozen in liquid nitrogen immediately. The samples were ground to powder by shaking and extracted by 2 mL ethyl acetate with 20 μg/mL dodecane as internal standards overnight. The sample was filtered and the filtrate was dried over anhydrous Na$_2$SO$_4$ and then analyzed by GC/MS. The parameters of GC/MS were the same as described in Example 1.

Figure 6:
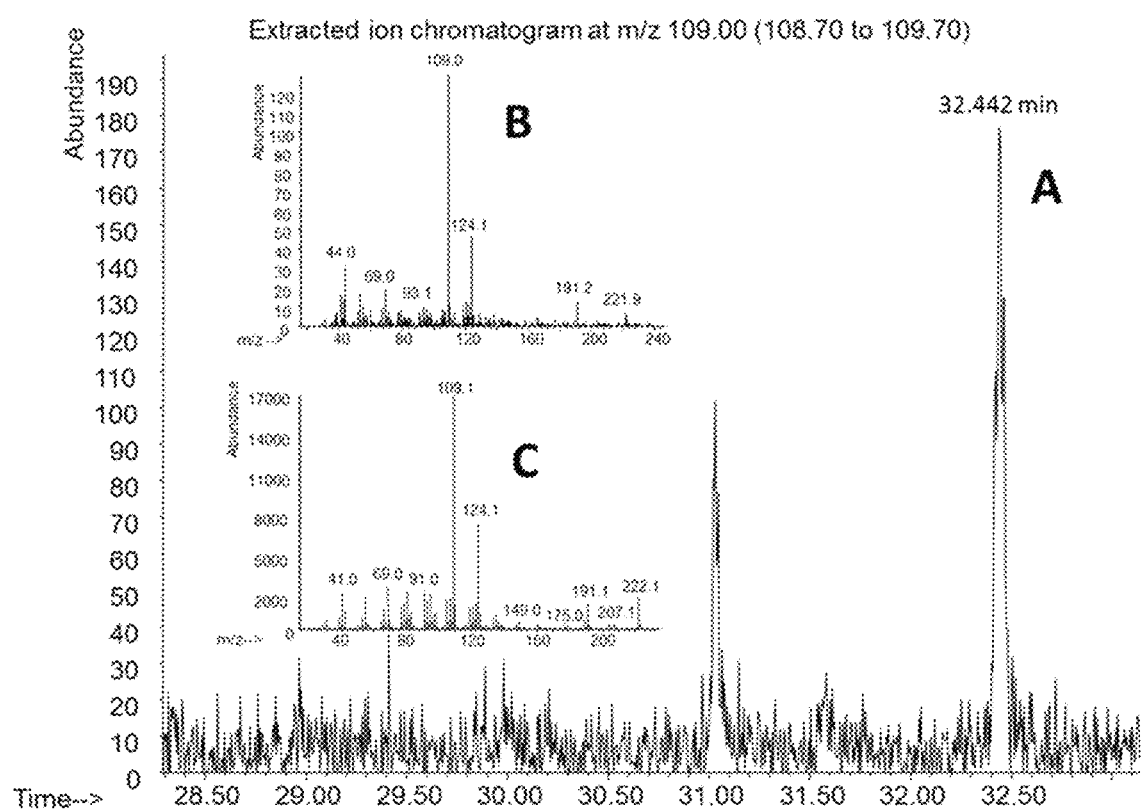
FIG. 6. Shows GC/MS analysis (extracted ion chromatogram at m/z 109) of transient expression experiment of the isolated drimenol synthase on tobacco leaves. B. Mass spectrum of the peak at 32.442 min is drimenol. C. Mass spectrum of authentic sample of drimenol.

In this tobacco transient transformation experiment, PaTPS1 produced drimenol as the only detectable product based on comparison to data recorded from an authentic standard (FIG. 6). The yield of drimenol in this experiment was calculated based on the internal standard as 3.9 μg drimenol per gram of fresh tobacco leaves.

```
                      Sequence Listings

SEQ ID NO: 1
Coding DNA sequence of PaTPS1:
ATGTCTCTTCCCGTCTCAGTAGCTAATCAGCCACCGGCGAAATGTAAACA
AGAGGTTATTCGCAATACAGCAAATTTCCCCCGTGGTATTTCCGCTCATC
AGTTCATCACTTACACTCCTCAAGATGAGGAAACTCGTGCGCATATAGTA
CAAGAGATTGAAGAACTGAAAGAAATTGTAAGAACAGAGGTGATGACACT
TGTTGGTATACCTTCACAACAACTCAAGCTTGTTGATGCAATCCAACGCC
TTGGTGTGGGATACCACTTTCAGAAGGAGATAGATGAAGCCTTACACCAA
CTGTATGATACATATGGTCATGGCCAAGATGAAGATCTCTTCACAGTTGC
TCTTTGGTTCAGACTTCTAAGACAACAAGGGTATAATGTTTCATGTGACA
TATTCAACAAATTCACCGACGACAAGGGAAACTTCAAGGAATGCTTGGTT
CAAAATGTGGAGGGCATGGTAGCCTTGTACGAAGCAACGCATCTCAGAGT
GCATGGAGAAGATGTACTTGAAGCAGCACTCACTTTTACAACCATTCACC
TTAAGGCCTTGGCAACTCATCTTGCAAGCCATCCCCTTAGAGCACTAGTG
AATCGTGCCCTAGAACAGCCTACCTATAAGGGTGTACCTAGGCTGGAGGC
AAGACATTATATATCTTTCTATCAACAAGAGCAATTGCATGAAAGCTT
TACTGAGACTTGCCAAGTTAGATTTTAACCTACTACAATCATTGCACAAA
AAGGAGCTATCGGAGGTCGCTAGATGGTGGACAAAAGTAAACTTTGAAAA
CAAGTTACCTTTCGTGAGAGACAGGTGGTGGAGAGTTACTTTTGGGGAT
TGGGAGATTATTTTGAGCCTGAGCACTCCATTGCTAGAATGATATTAAGC
AAAATAATCGCCCTAGTAACGGTTATGGATGATATTTATGACGCATATGG
TACACTGGAAGAACTCGAGCTATTTACAGATGCAGTTCAAAGGTGGGATA
TCAACTGCACCCAACAACTCCCAGAATACATTAAAGTGTTTTTTCAGGCA
ATGTTAGATGCATACGAAGAGATTGAAGAAGAATTATCTAACGAACCTGG
ACGAACATATCGTGTTCATTATGCAATAGAAGCCATGAAAATACAAGCCC
AAGCATACCTTGCTGAAACAAAATGGTCTAATGAAAAGTATGTACCGACA
TTTGAGGAGTATATGGATAATGCACGATTAAGCGCAGGTTACTTCATGCT
TACAGTCATATCTTTTCTTTTTATGGGGGAAGACGCGACAAAAGATTCAT
TTGATTGGCTGTTCAACGACCCTAAGATTCTTAGAGCCTCATCAATCATT
ACCAGGCTCATGGATGACATAGTTTCTCATAAGTTTGAGCAAGAGAGAGG
ACATGTTGCATCATCCGTTGAGTGTTACATGAAGCAACACAATGTTTCGG
AGCAACAAACATATCAAGAGTTTCAAATGAAAATTGTGGAGGGATGGAAA
GATCTAAATCAGGCATTACTCATACCTACTGATGCATCGATTCCTCTCCT
TACTCGTATCCTTAATTTTACACGCTTTATGGATGTTAACTACAAGGAAC
GAGATGAATTCACACATGTTGGAGACGTTTTAAAAGATCGAATTGCATTG
TTACTAATTGATCCCATCCCAATATGA SEQ ID NO: 2
Amino acid sequences of PaTPS1:
MSLPVSVANQPPAKCKQEVIRNTANFPRGISAHQFITYTPQDEETRAHIV
QEIEELKEIVRTEVMTLVGIPSQQLKLVDAIQRLGVGYHFQKEIDEALHQ
INDTYGHGQDEDLFTVALWFRLLRQQGYNVSCDIFNKFTDDKGNFKECLV
QNVEGMVALYEATHLRVHGEDVLEAALTFTTIHLKALATHLASHPLRALV
NRALEQPTYKGVPRLEARHYISFYQQEQLHDKALLRLAKLDFNLLQSLHK
KELSEVARWWTKVNFENKLPFVRDRVVESYFWGLGDYFEPEHSIARMILS
KIIALVTVMDDIYDAYGTLEELELFTDAVQRWDINCTQQLPEYIKVFFQA
MLDAYEEIEEELSNEPGRTYRVHYAIEAMKIQAQAYLAETKWSNEKYVPT
FEEYMDNARLSAGYFMLTVISFLFMGEDATKDSFDWLFNDPKILRASSII
TRLMDDIVSHKFEQERGHVASSVECYMKQHNVSEQQTYQEFQMKIVEGWK
DLNQALLIPTDASIPLLTRILNFTRFMDVNYKERDEFTHVGDVLKDRIAL
LLIDPIPI SEQ ID NO: 3
The DNA sequence of CaMV35S promoter
GAATTCCCATGGAGTCAAAGATTCAAATAGAGGACCTAACAGAACTCGCC
GTAAAGACTGGCGAACAGTTCATACAGAGTCTCTTACGACTCAATGACAA
GAAGAAAATCTTCGTCAACATGGTGGAGCACGACACGCTTGTCTACTCCA
AAAATATCAAAGATACAGTCTCAGAAGACCAAAGGGCAATTGAGACTTTT
CAACAAAGGGTAATATCCGGAAACCTCCTCGGATTCCATTGCCCAGCTAT
CTGTCACTTTATTGTGAAGATAGTGGAAAAGGAAGGTGGCTCCTACAAAT
GCCATCATTGCGATAAAGGAAAGGCCATCGTTGAAGATGCCTCTGCCGAC
AGTGGTCCCAAAGATGGACCCCCACCCACGAGGAGCATCGTGGAAAAAGA
AGACGTTCCAACCACGTCTTCAAAGCAAGTGGATTGATGTGATATCTCCA
CTGACGTAAGGGATGACGCACAATCCCACTATCCTTCGCAAGACCCTTCC
TCTATATAAGGAAGTTCATTTCATTTGGAGAGGACAGGGTACC SEQ ID NO: 4
The DNA sequence of OCS terminator
CTGCAGGCATGCCCTGCTTTAATGAGATATGCGAGACGCCTATGATCGCA
TGATATTTGCTTTCAATTCTGTTGTGCACGTTGTAAAAAACCTGAGCATG
TGTAGCTCAGATCCTTACCGCCGGTTTCGGTTCATTCTAATGAATATATC
ACCCGTTACTATCGTATTTTTATGAATAATATTCTCCGTTCAATTTACTG
ATTGTCCAAGCTT SEQ ID NO: 5
The optimized DNA sequence of GgFPS
ATGCAACCACACCATCATCACAAAGAAGGAAGAATGCACAAGTTTACTGG
AGTTAACGCAAAGTTTCAACAGCCTGCTCTCAGAAATCTTTCTCCTGTTG
TGGTTGAAAGAGAGAGGGAAGAGTTTGTGGGATTTTTCCCTCAAATTGTT
AGAGATTTGACTGAAGATGGAATCGGTCATCCAGAAGTGGGAGATGCAGT
TGCTAGGCTCAAGGAAGTTTTACAGTATAATGCTCCTGGAGGTAAATGTA
ACAGAGGACTCACAGTGGTTGCTGCATACAGGGAATTATCTGGACCAGGT
CAAAAGGATGCTGAGTCACTTAGATGTGCATTGGCTGTGGGATGGTGCAT
CGAGCTTTTCCAGGCATTTTTCTTGGTTGCTGATGATATTATGGATCAAT
CACTCACCAGAAGGGGACAGTTATGTTGGTATAAGAAAGAAGGAGTTGGT
CTTGATGCTATTAATGATAGTTTTCTTTTGGAGTCTTCAGTGTACAGAGT
TTTGAAGAAATATTGTAGACAAAGGCCTTACTACGTTCATCTCTTAGAAC
TTTTCTTGCAAACTGCATACCAGACAGAGTTGGGACAGATGCTCGATCTT
ATTACAGCTCCAGTGTCAAAGGTTGATCTCTCACACTTTAGTGAAGAGAG
ATATAAGGCAATCGTTAAGTACAAAACCGCTTTCTACAGTTTCTACCTTC
CTGTGGCTGCTGCTATGTATATGGTTGGTATAGATTCTAAGGAAGAGCAT
GAAAACGCAAAAGCTATACTTTTGGAAATGGGAGAGTACTTCCAAATACA
GGATGATTACCTTGATTGCTTCGGAGATCCTGCTTTGACCGGAAAGGTTG
```

GTACTGATATCCAAGATAATAAGTGTTCTTGGCTCGTGGTTCAATGCTTA
CAGAGAGTTACACCTGAACAAAGGCAGCTCTTAGAGGATAACTATGGAAG
AAAGGAACCAGAGAAAGTGGCAAAGGTTAAAGAATTGTACGAGGCTGTTG
GTATGAGAGCAGCTTTCCAACAGTATGAAGAGAGTTCTTACAGAAGGCTT

CAAGAATTGATCGAGAAACACTCAAACAGACTCCCTAAAGAAATCTTCCT
CGGACTCGCTCAGAAAATCTACAAAAGGCAAAAATGATAA

What is claimed is:

1. A method of producing drimenol comprising:
   i) contacting an acyclic farnesyl diphosphate (FPP) precursor with a polypeptide having drimenol synthase activity and having at least 90% sequence identity to SEQ ID NO: 2 or comprising SEQ ID NO:2 to produce drimenol; and
   ii) isolating the drimenol.

2. The method as recited in claim 1, comprising contacting the drimenol with at least one enzyme to produce a drimenol derivative.

3. The method as recited in claim 1, comprising converting the drimenol to a drimenol derivative using a chemical synthesis.

4. The method as recited in claim 1, further comprising, prior to step i), transforming a host cell or non-human organism with a nucleic acid comprising a nucleotide sequence encoding a polypeptide having drimenol synthase activity comprising an amino acid sequence having at least 90% sequence identity to SEQ ID NO: 2 or comprising SEQ ID NO:2 and culturing the host cell or organism under conditions that allow for the production of the polypeptide.

5. The method recited in claim 4, wherein the cell is a prokaryotic cell.

6. The method as recited in claim 4, wherein the cell is a bacterial cell.

7. The method as recited in claim 4, wherein the cell is an eukaryotic cell.

8. The method as recited in claim 7, wherein the eukaryotic cell is a yeast cell or a plant cell.

9. The method of claim 1, wherein the polypeptide has at least 95% sequence identity to SEQ ID NO: 2.

10. The method of claim 4 wherein the nucleotide sequence encodes a polypeptide having drimenol synthase activity and comprising an amino acid sequence having at least 95% sequence identity to SEQ ID NO: 2.

* * * * *